United States Patent
de la Torre et al.

(10) Patent No.: US 6,315,770 B1
(45) Date of Patent: Nov. 13, 2001

(54) LAPAROSCOPIC ACCESS PORT FOR SURGICAL INSTRUMENTS OR THE HAND

(75) Inventors: Roger A. de la Torre, St. Louis; James Stephen Scott, St. Charles, both of MO (US); Janine C. Robinson, Half Moon Bay, CA (US)

(73) Assignee: General Surgical Innovations, Inc., Palo Alto, CA (US)

( * ) Notice: Subject to any disclaimer, the term of this patent is extended or adjusted under 35 U.S.C. 154(b) by 0 days.

(21) Appl. No.: 09/371,695

(22) Filed: Aug. 10, 1999

Related U.S. Application Data

(63) Continuation of application No. 08/931,632, filed on Sep. 16, 1997.

(51) Int. Cl.$^7$ ............................................ A61B 17/00
(52) U.S. Cl. ............................... 606/1; 604/264; 606/205
(58) Field of Search .............................. 604/176, 264, 604/164.01, 164.02, 164.08, 171, 523, 533–539; 606/108, 213, 185, 1, 205–211

(56) References Cited

U.S. PATENT DOCUMENTS

| | | |
|---|---|---|
| 3,244,169 | 4/1966 | Baxter . |
| 3,685,509 * | 8/1972 | Bentall ............................ 604/176 |
| 4,024,872 | 5/1977 | Muldoon . |
| 4,188,945 | 2/1980 | Wenander . |
| 4,308,864 | 1/1982 | Small et al. . |
| 4,991,593 | 2/1991 | LeVahn . |
| 4,998,538 * | 3/1991 | Charowsky et al. .................. 128/856 |
| 5,196,003 * | 3/1993 | Bilweis ..................................... 606/1 |
| 5,213,114 | 5/1993 | Bailey, Jr. . |
| 5,248,307 | 9/1993 | Sokoloff . |
| 5,299,582 | 4/1994 | Potts . |
| 5,316,541 | 5/1994 | Fischer . |
| 5,336,193 * | 8/1994 | Rom et al. ............................ 604/171 |
| 5,366,478 | 11/1994 | Brinkerhoff et al. . |
| 5,368,545 | 11/1994 | Schaller et al. . |
| 5,385,560 | 1/1995 | Wulf . |
| 5,391,156 | 2/1995 | Hildwein et al. . |
| 5,407,427 | 4/1995 | Zhu et al. . |
| 5,423,848 | 6/1995 | Washizuka et al. . |
| 5,437,683 | 8/1995 | Neumann et al. . |
| 5,480,410 * | 1/1996 | Cuschieri et al. .................... 606/213 |
| 5,514,133 * | 5/1996 | Golub et al. .............................. 606/1 |

(List continued on next page.)

FOREIGN PATENT DOCUMENTS

| | | |
|---|---|---|
| WO95/07056 | 3/1995 | (WO) . |
| WO95/22289 | 8/1995 | (WO) . |
| WO95/27445 | 10/1995 | (WO) . |
| WO95/27468 | 10/1995 | (WO) . |

OTHER PUBLICATIONS

Supplementary European Search Report, EP 96 93 3937, Oct. 2, 1998.

Inside Surgery, Medical Data International, vol. II, Jul., 1994, No. 1, pp. 117–120.

*Primary Examiner*—Glenn K. Dawson
(74) *Attorney, Agent, or Firm*—Fish & Richardson P.C.

(57) ABSTRACT

A flexible, fluid-tight envelope provides access for a hand and surgical instruments through a body tissue incision while maintaining insufflation pressure or a pneumoperitoneum within the body. The envelope is transparent and has an interior volume with opposite proximal and distal ends. A first opening in the envelope at the proximal end adjoins the incision in the body tissue and is secured and sealed to the body tissue. The second opening at the envelope distal end is provided with a closure member that seals closed the second opening on itself or around the forearm of a surgeon or a surgical instrument inserted into the interior volume of the envelope. An access port is provided at the first opening in the envelope. The access port comprises a housing containing a valve element that is selectively opened and closed to provide access to the tissue incision while maintaining insufflation pressure in the body cavity.

16 Claims, 11 Drawing Sheets

U.S. PATENT DOCUMENTS

| | | |
|---|---|---|
| 5,524,644 | 6/1996 | Crook . |
| 5,526,536 | 6/1996 | Cartmill . |
| 5,531,758 | 7/1996 | Uschold et al. . |
| 5,634,911 * | 6/1997 | Hermann et al. .................... 604/256 |
| 5,636,645 | 6/1997 | Ou . |
| 5,640,977 | 6/1997 | Leahy et al. . |
| 5,653,705 | 8/1997 | de la Torre et al. . |
| 5,672,168 * | 9/1997 | De La Torre et al. ................. 606/1 |

* cited by examiner

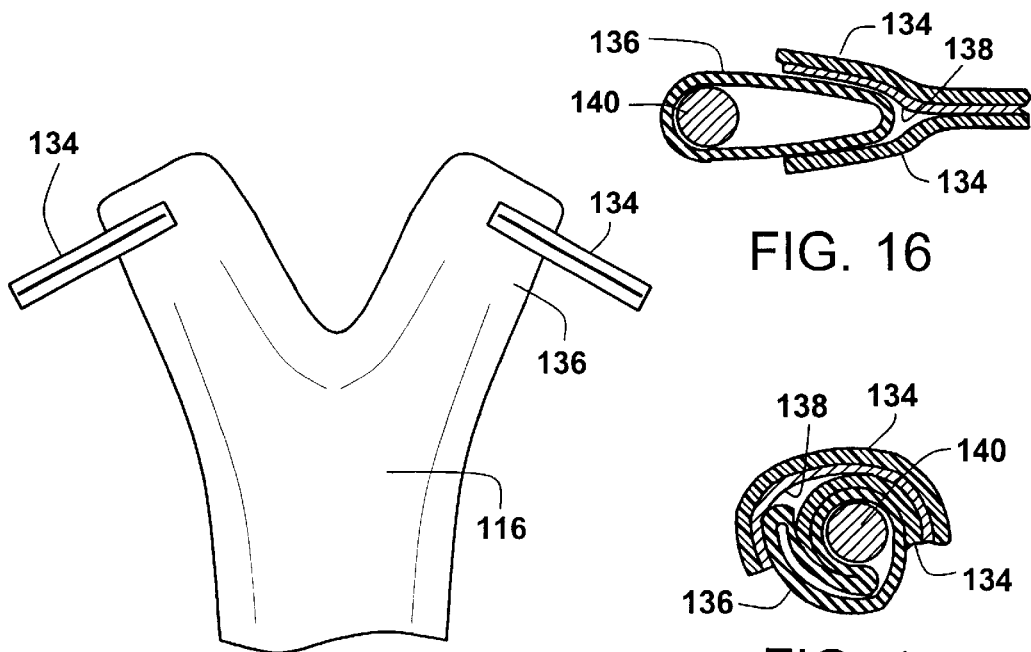
FIG. 15
FIG. 16
FIG. 17
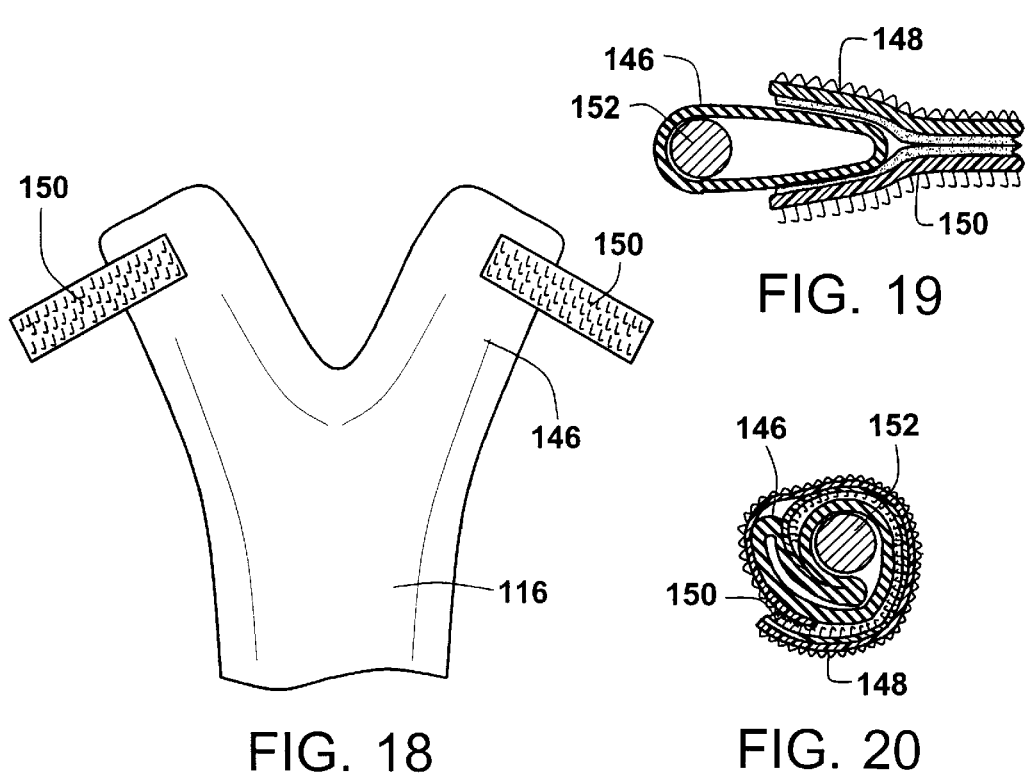
FIG. 18
FIG. 19
FIG. 20

LAPAROSCOPIC ACCESS PORT FOR SURGICAL INSTRUMENTS OR THE HAND

This application is a continuation of Ser. No. 08/931,632 filed Sep. 16, 1997.

BACKGROUND OF THE INVENTION (1) Field of the Invention

The present invention pertains to an apparatus employed as an access port in minimally invasive surgery that enables the insertion of instruments or the hand through a small incision in body tissue while maintaining the insufflation pressure within a body cavity.

(2) Description of the Related Art

Minimally, invasive surgery, such as laparoscopy, despite its beneficial aspects, has some disadvantages. Surgery of this type involving the use of surgical instruments manipulated through trocars or cannula inserted through body tissue to a surgery site within a body cavity-requires a great deal of manual dexterity and hand-eye coordination of the surgeon. Many years of practice are required before the surgeon develops a comfortable level of agility in manipulating surgical instruments inserted through trocars to the surgical site while observing the movements of the instruments through a laparoscope. Until this level of familiarity with surgery techniques is developed by the surgeon, minimally invasive surgery requires significantly more of the surgeon's time than would the same operation being performed in an open incision of the body.

Additionally, the need to maintain a pneumoperitoneum or insufflation pressure within the body cavity at the surgery site while instruments are removed from and inserted through trocars during surgery increases the time required for performing an operation by minimally invasive surgery over that required for performing the same operation through an open incision in the body.

It is an object of the present invention to provide a surgical apparatus and its method of use that assist the surgeon in performing minimally invasive surgery by providing an access port through body tissue to a body cavity at the surgery site which enables insertion of surgical instruments or the surgeon's hand through the access port while maintaining the insufflation pressure or pneumoperitoneum within the body cavity.

SUMMARY OF THE INVENTION

The surgical apparatus of the present invention is basically comprised of a flexible, fluid-tight envelope having a hollow interior and first and second openings at opposite proximal and distal ends of the envelope. In the preferred embodiment, the envelope is transparent. An access port, comprised of a pair of tubular collars in one embodiment, is secured to the opening at the proximal end of the envelope. The collars have coaxial interior bores and are connected to each other for relative rotation. The collars are provided with means for securing the collars to body tissue with the interior bores of the collars adjoining an incision through the tissue.

The distal end of the envelope is provided with means for selectively closing and sealing the second opening, or for opening the second opening to enable insertion of an instrument or the surgeon's hand into the envelope interior. With an instrument or the surgeon's hand inserted through the second opening, the means for sealing the opening is then secured around the envelope distal end and the instrument or hand to prevent the escape of insufflation pressure from the body cavity through the incision and the envelope. Several means of sealing closed the second opening of the envelope are provided including a slit second opening in the resilient material of the envelope that closes the opening in its at rest condition and is opened by stretching the material of the envelope. Various types of bands including elastic cords, strips containing malleable wire, and strips of hook and loop fastener material such as Velcro® are also secured around the distal end of the envelope to close and seal the envelope second opening.

Various embodiments of the concentric collars at the envelope proximal end are also employed in sealingly securing the envelope to the body tissue adjoining the tissue incision. These embodiments include a tapered portion of one of the collars which is wedged into the tissue incision to provide the sealed connection of the envelope to the tissue. A further embodiment employs an annular rim on one of the collars which is inserted through the incision to underlie the body tissue surrounding the incision. A panel having a circular center opening is then positioned over the collar and against the exterior of the body tissue to sandwich the tissue between the collar rim and the panel and thereby provide the sealed connection of the collars to the body tissue with the collars' interior bores adjoining the tissue incision. The embodiments of the collars are constructed of flexible plastic material that enables the collars to be clamped closed by a conventional grasper or forcep, thereby sealing closed the interior bores of the collars and enabling substitution of various embodiments of the envelope on the collars. A further embodiment of the collars is provided with a removable cap that closes over the collar interior bore sealing it closed.

In additional embodiments of the access port, the access port is comprised of a closure housing having an access opening extending through the housing that provides access to the incision surrounded by the housing. A valve element is provided on the housing that is selectively opened to provide access to the incision through the housing access opening, and closed preventing access to the incision through the access opening and maintaining the insufflation pressure within the body cavity. Various embodiments of the valve element are employed in the closure housing. These embodiments include a tethered plug that seats within the access opening to seal closed the opening, a sliding gate having an inlet opening that is aligned with the access opening in one position of the gate and displaced from the access opening in a second position of the gate, a compressible, resilient annular ring that has an inlet opening that is constricted closed when the ring is compressed and resiliently opens when the compression on the ring is relieved, and an iris valve comprised of a tubular sleeve that is twisted to constrict the sleeve to its closed position blocking the access opening of the closure housing. In each of these embodiments of the closure housing, various different embodiments of the envelope are employed.

One embodiment of the envelope has a general Y-shaped configuration with three projecting arms including one proximal arm and two distal arms. The proximal arm is provided with the first opening secured to the pair of collars and the two distal arms are provided with second and third openings and means on the distal arms for closing their openings as in the previously described embodiment of the envelope.

Further embodiments of the envelope have a tubular sleeve configuration with a first end of the sleeve secured around the exterior of the access port housing. The opposite end of the envelope sleeve is provided with one or more openings for insertion of the surgeon's hand and/or a surgical instrument into the envelope. Various mechanisms are provided for securing the envelope opening around the arm of the surgeon. In a further embodiment, the envelope is formed as an inverted glove having five fingers that depend into the interior volume of the envelope. The surgeon's fingers are inserted into the fingers in order to manipulate a surgical instrument contained in the interior of the envelope. A still further embodiment of the envelope sleeve employs a suction ring that is secured to the body tissue around the access port housing.

In use of each of the embodiments of the invention, an incision is made in the body tissue and the access port is secured to the body tissue with the center bore of the access port adjoining the tissue incision. The valve element of the access port housing is closed and the second opening of the envelope is sealed closed. The body cavity at the site of the surgery to be performed is then insufflated. The sealed connection of the access port to the body adjoining the incision and the sealed closure of the envelope second opening maintains the insufflation pressure within the body cavity while providing an access port for insertion of instruments or the surgeon's hand into the body cavity.

Insertion of an instrument or the surgeon's hand into the body cavity is accomplished by releasing the sealed closure of the envelope second opening and inserting the instrument or hand into the envelope interior through the second opening. The second opening is then again sealed closed around the instrument or forearm of the hand inserted into the envelope. The instrument or hand may then be inserted through the interior bore of the access port secured to the body with the sealed closure of the second opening around the instrument or hand maintaining the insufflation pressure within the body cavity. Alternatively, the valve element of the access port may be closed around the instrument or hand to maintain the pressure in the body cavity.

BRIEF DESCRIPTION OF THE DRAWINGS

Further objects and features of the present invention are revealed in the following detailed description of the preferred embodiment of the invention and in the drawing figures wherein:

FIGS. 15–17 show a further embodiment of the envelope of the invention;

FIGS. 18–20 show a further embodiment of the envelope of the invention;

DESCRIPTION OF THE PREFERRED EMBODIMENTS

Figure 1:
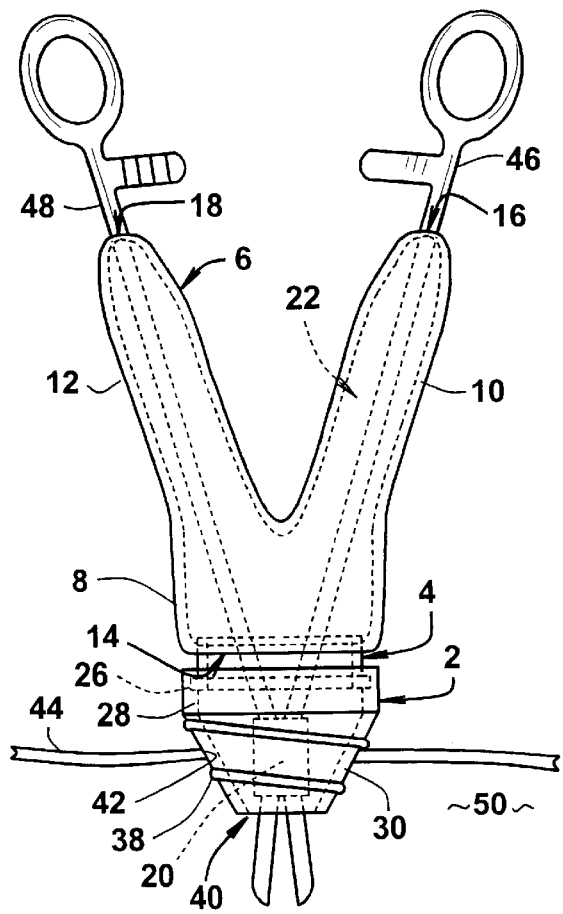
FIG. 1 shows a first embodiment of the invention in its operative position sealed to an incision made in body tissue and projecting into a body cavity.

A first embodiment of the apparatus of the invention is shown in FIG. 1 of the drawing figures. In this embodiment the access port housing is generally comprised of a first collar 2, a second collar 4, and a flexible, fluid-tight envelope 6. In the preferred embodiment of the invention, the three primary component parts set forth above are all constructed of flexible, resilient plastic materials. However, it should be understood that the apparatus of the invention may be constructed of various different types of materials acceptable for use in surgical instruments. Furthermore, the relative dimensions of the component parts of the invention shown in the drawing figures are illustrative only and should not be interpreted as limiting. The apparatus of the invention can be constructed in various different sizes without departing from the intended scope of the invention.

Preferably, the material of the envelope 6 is also transparent to enable the surgeon to observe the manipulation of an instrument or the surgeon's hand in the envelope. For example, the envelope could be formed from two overlapping layers of urethane film that are heat sealed together at their edges. Other equivalent materials and methods of construction may be employed. The envelope 6 has a general Y-shaped configuration with a first arm 8 at a proximal end of the envelope and second 10 and third 12 arms at the opposite distal end of the envelope. A first opening 14 is provided at the end of the envelope first arm 8 and the second collar 4 is received in the first opening. The second collar 4 and the envelope first arm are permanently secured together providing a sealed connection between the collar and envelope. Alternatively, the envelope first arm could overlap the top of the collar and be secured thereto by an elastic band or a length of suture tied around the arm and collar. The ends of the second and third arms 10, 12 are also provided with respective second 16 and third 18 openings therethrough. Means are provided at the ends of the second and third arms 10, 12 for selectively closing and sealing the respective second and third openings 16, 18. The manner of closing the second and third openings will be described in more detail with reference to later embodiments. The closures at the second and third openings 16, 18 enable these openings to be closed and sealed around surgical instruments such as the forceps 20 shown in FIG. 1. Alternatively, in a larger version of the apparatus shown in FIG. 1, the surgeon's hand and forearm can be inserted through the second opening 16 and the surgical instrument inserted into the envelope interior 22 through the third opening 18 to be grasped by the surgeon within the envelope. The second opening 16 may then be secured around the forearm of the surgeon and the third opening 18 closed and sealed to prevent the escape of insufflation pressure through the second and third openings in use of the apparatus.

The second collar 4 has a cylindrical configuration with a hollow, cylindrical interior bore extending therethrough. The interior bore 24 of the collar communicates with the interior volume 22 of the envelope, opposite its connection to the envelope 6, the second collar has an annular flange 26 that extends around its exterior surface.

The first collar 2 is formed of two sections, a first section 28 having a cylindrical configuration and a second section 30 having a tapering configuration. The first section 28 has a cylindrical interior bore 32 with an annular groove 34 formed therein. The annular groove 34 is dimensioned to receive the annular flange 26 of the second collar, thereby providing a sealed rotatable connection between the first and second collars. As seen in FIG. 1, the second section 30 is formed as a skin screw which screws into and forms a seal of the access port housing attaching it to the incision in the skin. The section has a tapering interior bore 36 and a tapering exterior surface over which extends a helical thread 38. The threads are screwed into an incision in the skin tissue to sealingly attach the access port over the incision. The first collar second section 30 tapers to an access opening 40 that provides access from the envelope interior volume 22 through the interior bores of the first and second collars 2, 4.

Referring to FIG. 1, in use of this first embodiment of the apparatus of the invention, an incision 42 is first made through body tissue 44. The first collar 2 is then secured in the incision by first inserting the tapered section 30 of the collar into the incision 42 and rotating the collar, causing the helical thread 38 to pull the collar 2 further into the incision. The incision 42 in the body tissue 44 is stretched around the exterior of the first collar 2 as the collar is turned and effectively screwed into the incision. The snug fit of the first collar tapered section 30 in the incision 42 secures the apparatus to the body tissue and seals the connection of the apparatus to the tissue. Alternatively, the first collar, without the skin screw, may be secured to the body tissue by adhesive tape, or may be sutured to the tissue. The first collar 2 may be provided with a cannula extension (not shown) from its access opening 40 to reach through all skin layers. The first collar 2 may be secured to the tissue 44 by its being wedged in the incision 42 with the second collar 4 and envelope 6 attached, or with the second collar and envelope removed. In the later case, the flexibility and resiliency of the first and second collars enables the second collar 4 to be later attached to the first collar 2 inserting the annular flange 26 of the second collar into the annular groove 34 of the first collar. The second and third openings 16, 18 of the envelope 6 are closed to seal the envelope interior volume 22. If so desired, an instrument such as the forcep 20 may first be inserted into the envelope interior through one of the first or second openings 16, 18 and then positioned in the envelope with each of its handles 46, 48 projecting through the first and second openings. The first and second openings are then sealed closed around the handles of the forcep.

Figure 3:
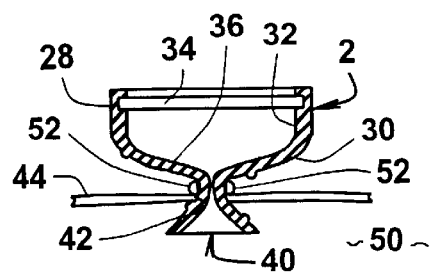
FIG. 3 is an in-section view of a collar of the FIG. 1 embodiment clamped closed.

Following the setup of the apparatus of the invention described above, insufflation pressure is then supplied to the body cavity 50. The insufflation pressure passes through the incision and also inflates the envelope. If it is later necessary to remove the forceps 20 or the envelope 6 for its replacement with another embodiment of envelope to be described later, the resilient material of the first and second collars 2, 4 enable the collars to be clamped closed with the jaws 52 of a surgical clamp as illustrated in FIG. 3. This seals closed the access port provided by the apparatus of the invention maintaining the insufflation pressure while the envelope is replaced on the first collar 2. Alternatively, the access port housing could be provided with a valve assembly, several embodiments of which will be described later.

Because insufflation pressure is low, typically 10 mm of mercury (Hg), various different types of valve assemblies may be employed in the first collar bore to maintain insufflation pressure in the body cavity. For example, an inflatable toroid-shaped balloon which closes at its inside diameter when inflated may be employed as the valve. Also, a foam disk having a center aperture which closes due to the resiliency of the foam may also be employed as the valve. In both examples, the flexibility of the balloon or foam allow insertion of the hand and/or instruments through the center opening. The resiliency of the balloon or foam causes the center opening to seal around the hand or instrument inserted through the opening, and causes the opening to seal closed once the hand or instrument is removed. Various other types of value structures may also be employed.

Figure 2:
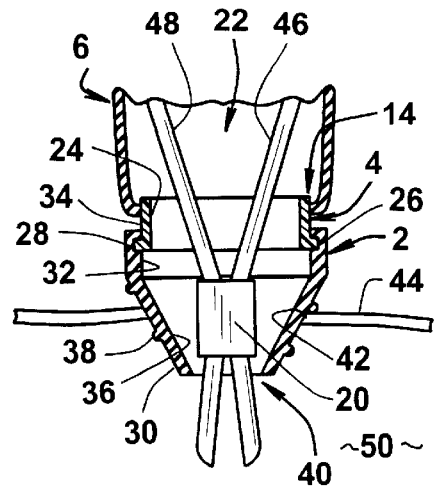
FIG. 2 is a partial, in-section view of the embodiment of FIG. 1.
Figure 4:
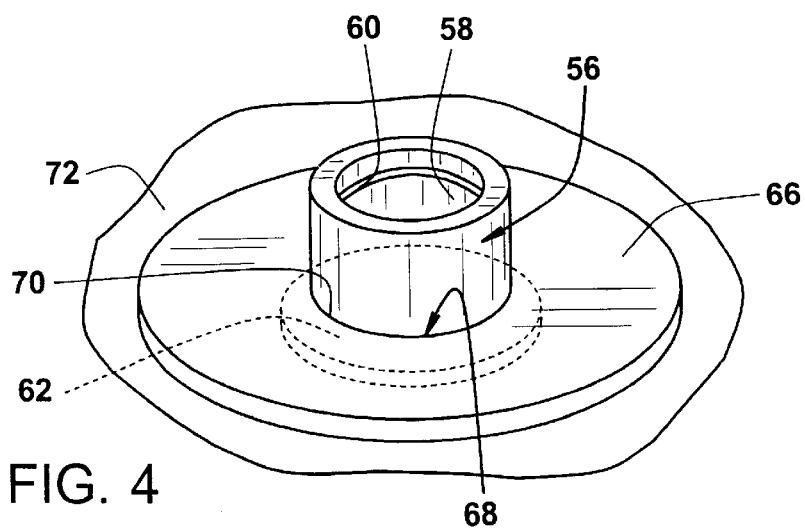
FIG. 4 is a perspective view of a second embodiment of one of the collars of the invention.

FIG. 4 shows an alternative to the first collar 2 of the apparatus of FIGS. 1–3. In FIG. 4, the first collar 56 again has a cylindrical configuration with a cylindrical interior bore 58 having an annular groove 60 dimensioned to receive the annular flange 26 of the second collar 4 of the apparatus of FIGS. 1–3. However, instead of a tapered section of a collar, this embodiment of the first collar has an annular rim 62 adjacent its access opening 64. A circular panel 66 having a circular center opening 68 is positioned over the collar 56 with the collar extending in a tight, friction fit through the panel opening 68. Together, the annular rim 62 and panel 66 secure this embodiment of the first collar 56 to the body tissue with the collar extending through the incision in the tissue.

Figure 5:
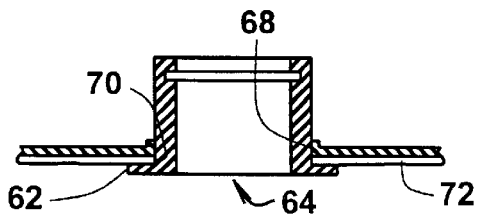
FIG. 5 is a cross section of the collar of FIG. 4.
Figure 6:
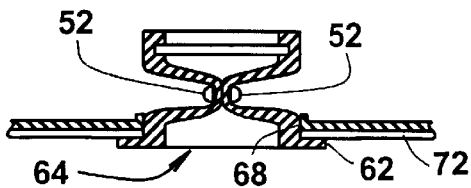
FIG. 6 is a cross section of the collar of FIG. 4 showing the collar clamped closed.

In use of the embodiment of FIGS. 4–6, the flexible resiliency of the material of a collar enables the collar rim 62 to be deformed and inserted through a small incision 70 made in the body tissue 72. The resiliency of the collar enables it to expand once inserted through the incision 70 so that the incision is stretched around the periphery of the collar 56 and the annular rim 62 extends beneath the body tissue surrounding the incision. The panel 66 is then positioned over the collar 56 with the collar inserted through the panel opening 68. With the panel pushed down over the collar, the tight-friction fit of the panel 66 around the collar secures the collar to the body tissue 72 and seals the incision between the collar rim 62 and the panel 66. With the collar in place, the second collar 4 and envelope 6 may then be attached to the first collar in preparation for use as described earlier with reference to the first embodiment.

Like the first collar of the first embodiment, the first collar embodiment of FIGS. 4–6 may also be sealed closed by crimping the collar between the jaws 52 of a surgical grasper as illustrated in FIG. 6, thereby sealing closed the collar interior bore 58 and maintaining the insufflation pressure in the body cavity when the envelope is removed from the collar.

Figure 7:
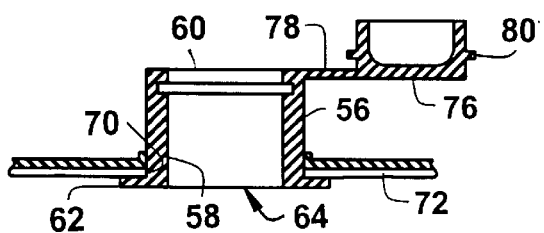
FIGS. 7 and 8 show a variant embodiment of the collar of FIG. 4.
Figure 8:
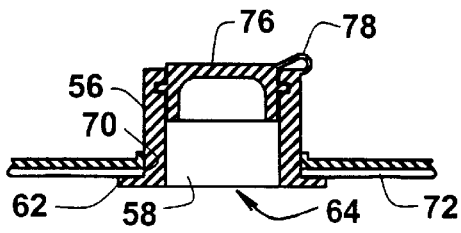

Alternatively, the first collar may be provided with a sealing cap 76 as shown in FIGS. 7 and 8. The cap 76 is connected by a flexible tether 78 to the collar 56. The cap 76 has an annular flange 80 around its periphery that is dimensioned to fit the annular groove 60 of the first collar with the cap inserted into the collar interior bore, thereby sealing closed the interior bore of the collar.

FIGS. 9–23 show various embodiments of the envelope, all of which may be employed with the first described embodiment of the first collar 2 shown in FIGS. 1–3 or the second described embodiment of the first collar 56 shown in FIGS. 4–8.

Figure 9:
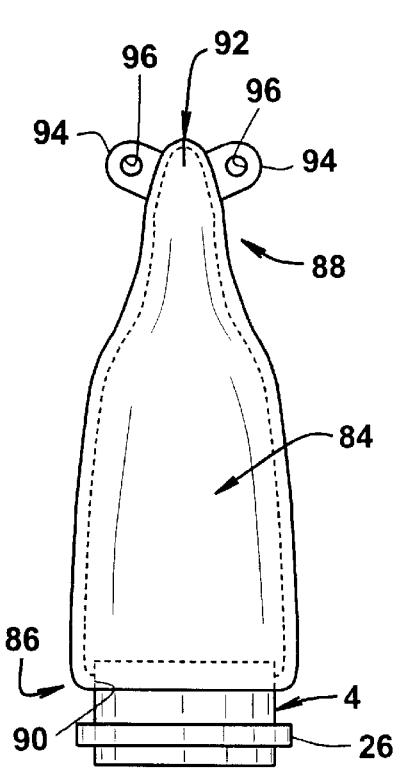
FIGS. 9 and 10 show a further embodiment of the envelope of the invention.
Figure 10:
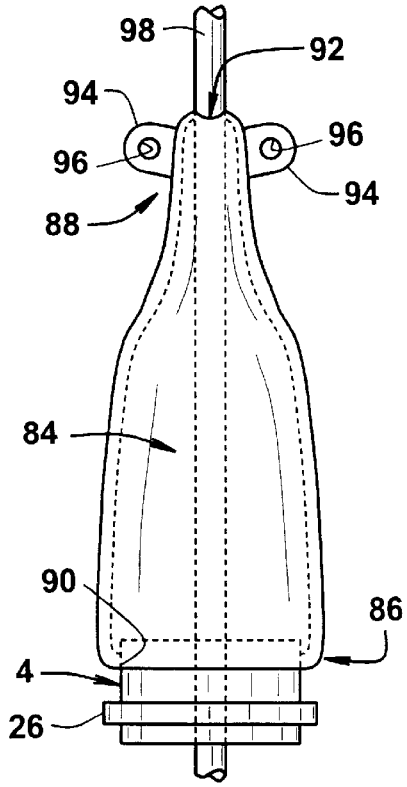

The embodiment of the envelope 84 shown in FIGS. 9 and 10 does not have the Y-shaped configuration of the first described embodiment of the envelope. The envelope 84 has opposite proximal 86 and distal 88 ends. The envelope proximal end 86 has a first opening 90 that is secured to a second collar 4 identical to the second collar of the first described embodiment. The connection between the envelope 84 and the second collar 4 is also identical to that of the first described embodiment. The material of the envelope 84 is transparent, flexible and fluid-tight as the first described envelope. However, this embodiment of the envelope employs a material that has resiliency enabling the material to be stretched from its at-rest configuration shown in FIG. 9.

The second opening 92 at the envelope distal end 88 is formed as a slit opening. In the at-rest condition of the envelope, the second opening 92 is closed. The resiliency of the envelope material is sufficient to maintain the second opening closed in its at-rest condition and prevent leakage of insufflation pressure, typically 10 mm of mercury (Hg), through the slit opening. A pair of ears 94 project from the envelope on opposite sides of the second opening 92. Each of the ears 94 has a hole 96 therethrough that can be engaged by a spreading tool to move the ears away from each other. Movement of the ears 94 away from each other stretches the slit opening 92 of the envelope open, enabling the insertion of instruments, such as the intermediate length of the surgical grasper 98 shown in FIG. 10, through the opening. The resiliency of the envelope material causes the slit opening 92 to close and seal around the grasper 98 when the ears 94 are released, thereby maintaining the insufflation pressure.

As in the first embodiment of the invention, the second collar 4 at the proximal end of the envelope 84 is provided with an annular flange 26 that engages in the annular groove of the first collar forming the sealed, rotating connection between the first collar and the envelope 84.

Figure 11:
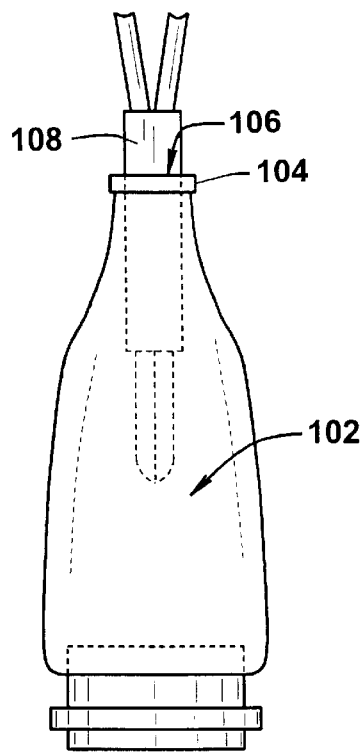
FIGS. 11 and 12 show a further embodiment of the envelope of the invention.
Figure 12:
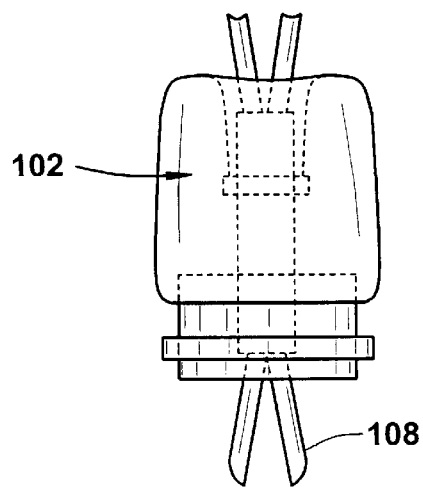

FIGS. 11 and 12 show an embodiment of the envelope 102 similar to the previously described embodiment of the envelope 84 of FIGS. 9 and 10. The difference between the embodiment of FIGS. 9 and 10 and that of FIGS. 11 and 12 is that the slit opening and ears of the previous embodiment are replaced by an elastic band 104 that surrounds the second opening 106 at the distal end of the FIG. 11 and 12 envelope embodiment. The remaining construction of the envelope 102 and second collar 4 remains the same as previously described embodiments. In the embodiment of FIGS. 11 and 12, the elastic band 104 is stretched open to enable insertion of an instrument, such as the forceps 108, into the envelope second opening 102. The band 104 is then allowed to contract around the forceps 108 near the hinge point or box lock to essentially seal the second opening 106 around the forceps and maintain insufflation pressure. As shown in FIG. 12, the flexibility of the envelope material enables the envelope to be folded back in through its interior when reaching into the incision with the forceps.

Figure 13:
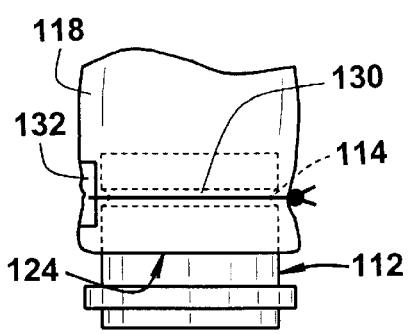
FIGS. 13 and 14 show a further embodiment of the envelope of the invention.
Figure 14:
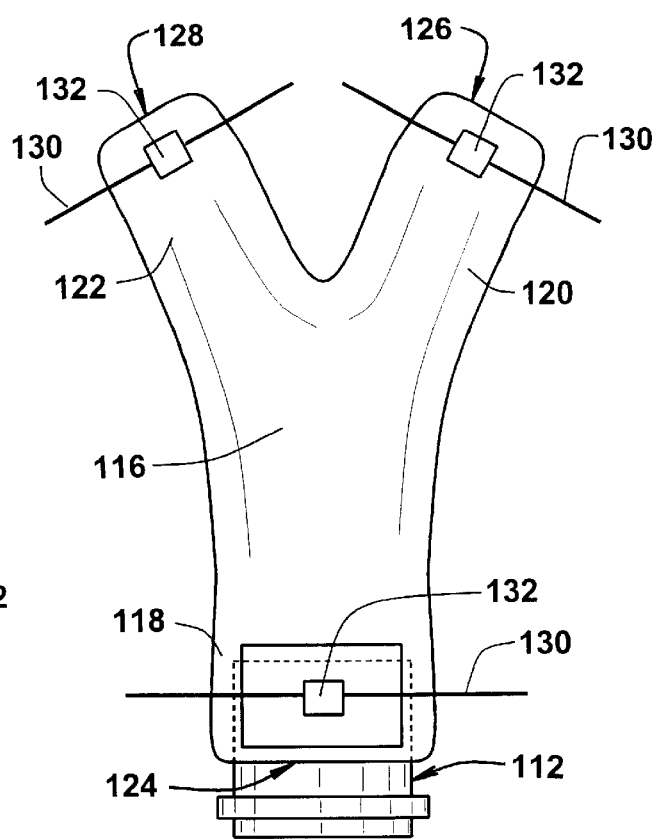

In the embodiment of the envelope shown in FIGS. 13 and 14, the second collar 112 varies only slightly from the second collar of the previously described embodiments in that it has an annular groove 114 formed around its exterior surface. The remaining construction of the second collar and the manner in which it connects to the first collar for relative rotation therewith remains the same.

Various embodiments of the envelope may be removably attached to the embodiment of the second collar 112 shown in FIG. 13. The envelope 116 shown in FIGS. 13 and 14 again has the general Y-shaped configuration of the first described embodiment including the proximal arm 18 and two distal arms 120, 122. The proximal arm 118 has a first opening 124 to the interior volume of the envelope and the distal arms 120, 122 have second and third openings 126, 128 to the envelope interior. Connected to the proximal and distal arms adjacent their openings are flexible bands, in this embodiment lengths of elastic cord 130 secured adjacent the openings by sections of adhesive tape 132.

In securing the proximal arm 118 to the second collar 112, the collar is inserted through the first opening 124 of the arm and the length of cord 130 is positioned adjacent the collar external groove 114. The length of cord is then tightly bound around the envelope proximal arm 118 overlying the collar exterior groove 114 securely connecting the proximal arm of the envelope to the collar. The connection of the envelope arm to the collar in this manner provides a sufficient seal between the arm and collar to maintain insufflation pressure. The second and third openings 126, 128 of the distal arms 120, 122 are sealed closed in the same manner. The second and third openings may be sealed closed upon themselves, or may be sealed closed around the forearm of the surgeon or around a surgical instrument by binding the cords 130 around the distal arms in the same manner as described with reference to the proximal arm of the envelope 116.

The embodiments of the envelope shown in FIGS. 15–20 are substantially identical to that shown in FIGS. 13 and 14 except that other closure means are employed in lieu of the cord 130 employed in the FIG. 13 and 14 embodiment.

In FIG. 15, two strips of adhesive tape 134 are secured to each of the envelope arms 136. A length of malleably metal 138, for example a length of wire, is sandwiched between the two pieces of tape. To close the openings at the ends of the two envelope distal arms 136, the tape containing the wire is wrapped around the arm and the instrument 140 inserted through the arm openings to securely seal the openings around the instrument as shown in FIGS. 17. If an instrument is not inserted through the arm opening, the tape containing the wire is merely wrapped around the arm to seal closed the opening. The wire within the tape maintains the tape in its wrapped configuration around the envelope arm.

FIGS. 18–20 show a further embodiment in which the cords and tape of the previously described embodiments are replaced by hook and loop fasteners, for example Velcro® type fasteners. As shown in the drawing figures, each of the envelope distal arms 146 has the Y backside of a hook fastener strip 148 and a loop fastener strip 150 secured thereto. Portions of the backsides of the hook and loop fastener strips are also secured together. To seal closed the arm opening around an instrument 152 inserted through the opening, the hook and loop fasteners are wrapped around the envelope distal arm and the instrument inserted through the opening of the arm. This causes the hook strip 148 to overlap the loop strip 150 and thereby seal closed the arm opening around the instrument 152.

Although only the envelope distal arms are shown in FIGS. 15–20, it should be understood that the tape and wire closure shown in FIGS. 15–17 and the hook and loop closure shown in FIGS. 18–20 may be employed to removably secure the proximal arm to the second collar in lieu of the elastic cord 130 disclosed in the embodiment of FIGS. 13–14. Still further, the envelope openings at the proximal and distal ends of the envelope may be sealed closed in other equivalent manners than those disclosed above.

Figures 21, 22:
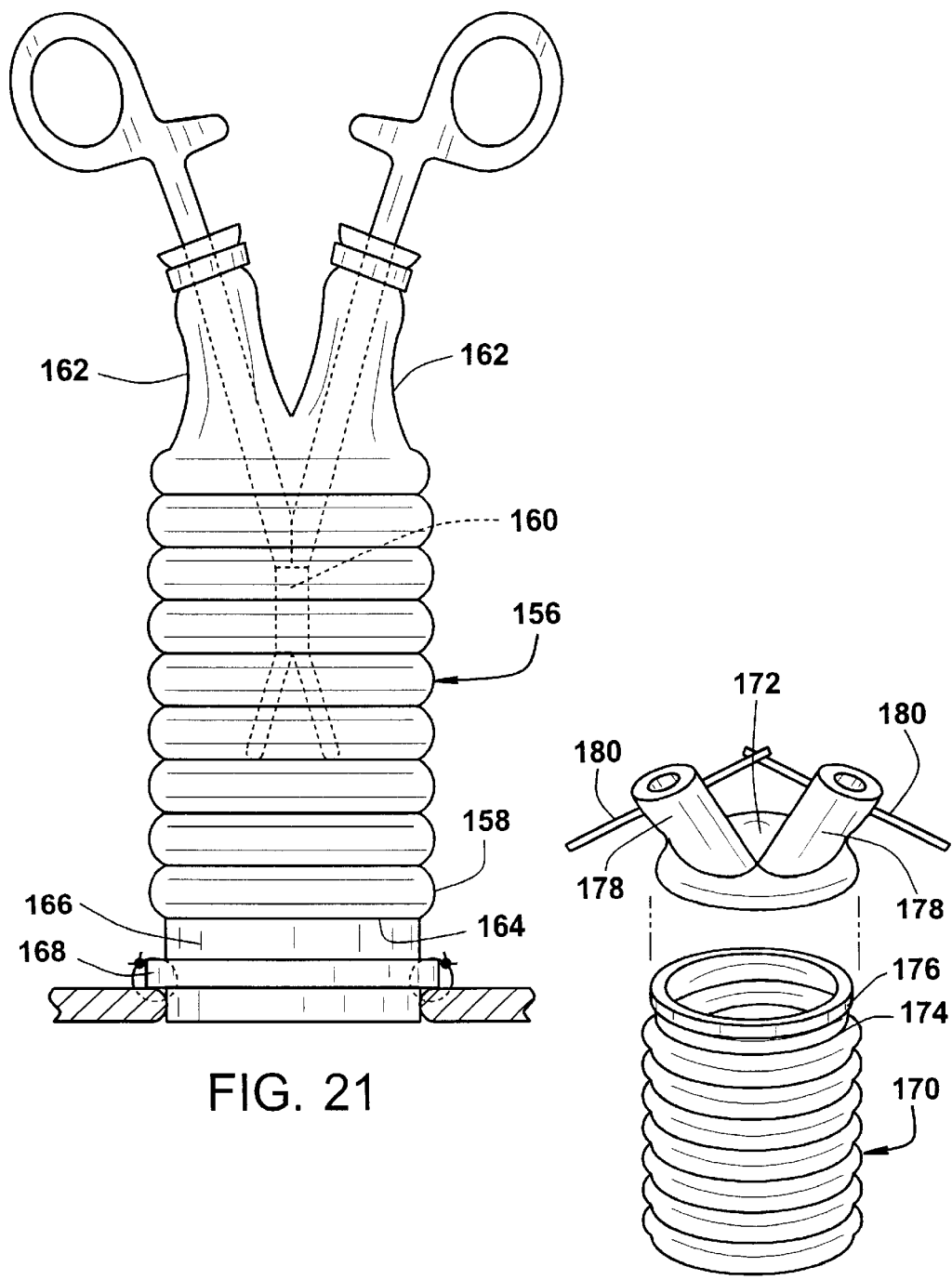
FIGS. 21–23 show a further embodiment of the envelope of the invention.

The envelope 156 of the FIG. 21 embodiment is similar to the previously described Y-shaped embodiments except that its first arm 158 is formed as a bellows with a plurality of pleats. The pleats formed in the first envelope arm 158 give it even more flexibility than the previously described embodiments and enable reaching deep into an incision with an instrument 160 by compressing the pleats of the bellows. Expanding the pleats of the bellows enables the instrument 160 to be withdrawn and spaced far from the incision with the expanding bellows pleats significantly increasing the interior volume of the envelope 156. The distal arms 162 of the envelope are secured and sealed to the handles of the instrument 160 in the same manner as any of the previously described embodiments. The proximal end of the envelope 164 is secured to a collar 166 that can be releasably attached to any of the previously described embodiments of the first collar. Additionally, the collar 166 can be secured directly to the body tissue surrounding the incision as shown in FIG. 21. The lower end of the collar is first inserted through the incision until the annular flange 168 of the collar abuts against the exterior surface of the tissue surrounding the incision. The collar may then be secured in place to the tissue incision by passing suture through the collar and the tissue surrounding the incision. Alternatively, the collar could be secured in place through the use of adhesive tape. In use of the collar in this manner, the lower end of the collar is extended to ensure that it reaches completely through the layer of skin tissue.

FIGS. 22 and 23 show a variation of the envelope of FIG. 21. In this embodiment, the envelope distal end has a circular cap 172 removable secured thereto. The cap is preferably constructed of a flexible plastic material and is provided with an interior annular groove (shown in dashed lines in FIG. 22) much the same as the annular groove provided in the first and second embodiments of the first collar 2, 56 described earlier. The distal end 174 of the envelope 170 has an annular flange 176 formed thereon dimensioned to mate in the annular groove on the interior of the cap 172. The insertion of the annular flange 176 into the cap annular groove provides a releasable, sealed connection between the envelope proximal end 174 and the cap 172.

Figure 23A:
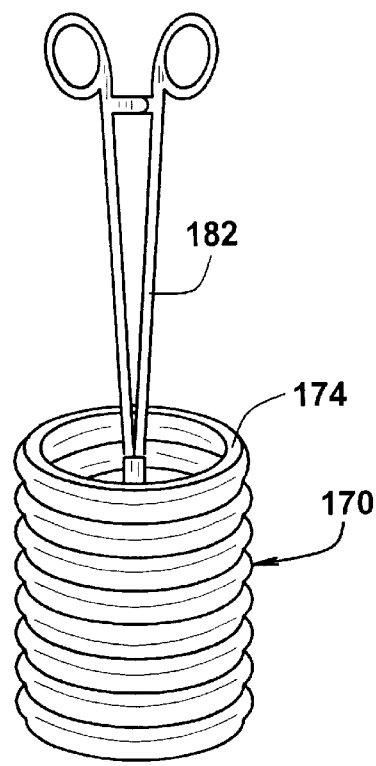
Figure 23B:
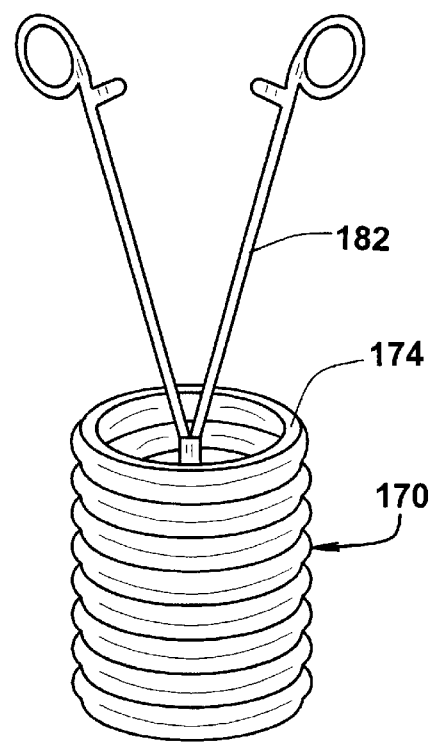
Figure 23C:
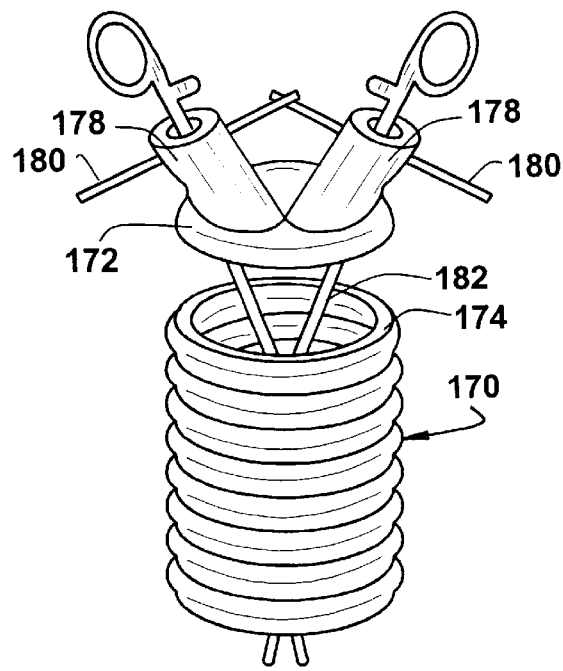
Figure 23D:
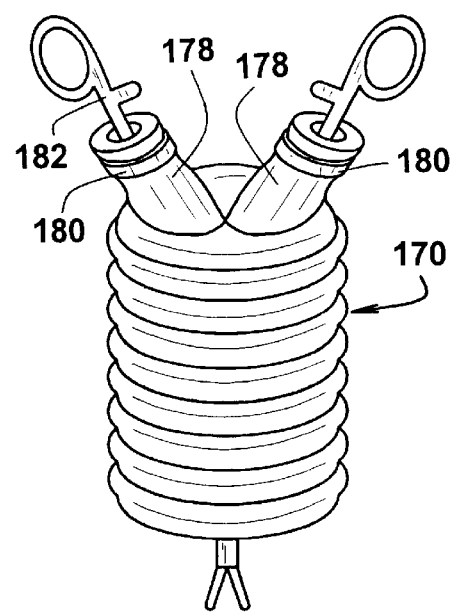

The cap 172 is also provided with a pair of distal arms 178. The arms 178 are also constructed of the flexible, resilient plastic material enabling the handles of an instrument to be inserted through the interiors of the arms as illustrated in FIG. 23C. Elastic cords 180 are secured to each of the arms 178 for securing the arms closed around the instrument handles as in the previous embodiments. Other equivalents of the cords 180 may also be employed in closing the arms 178 around the instrument handles.

By providing a detachable cap on the envelope, the pleated section of the envelope does not need to be very wide. The envelope can be much narrower if the instrument can be loaded into the envelope from the top. In this way, the handle rings of the instrument do not have to fit through the envelope. (See FIG. 23). Use of this embodiment of the invention is illustrated in FIGS. 23A–23D. The removable cap 172 is first removed from the proximal end of the envelope 170 exposing the envelope interior volume. The instrument 182 may then be inserted into the envelope. As shown in FIG. 23B, the interior volume of the envelope provides ample room for manipulation of the instrument. The cap 172 is then positioned over the instrument's handles inserting each of the handles through the arms 178 of the cap so that they project from the arms as illustrated in FIG. 23C. The cap 172 is then secured to the envelope distal end 174 by inserting the annular flange 176 into the interior annular groove of the cap as explained earlier. The cords 180 are next secured tight (e.g. by a simple half-hitch) around the arms 178 sealing the arms to the instrument handles. This embodiment of the invention is now ready for use in the same manner as the previously described embodiments.

Figure 24:
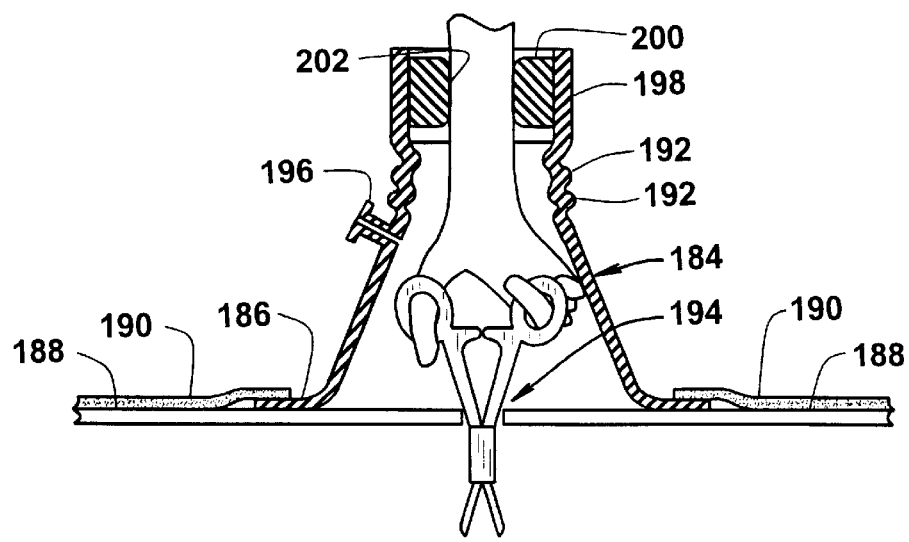
FIGS. 24 and 25 show a further embodiment of the invention.
Figure 25:
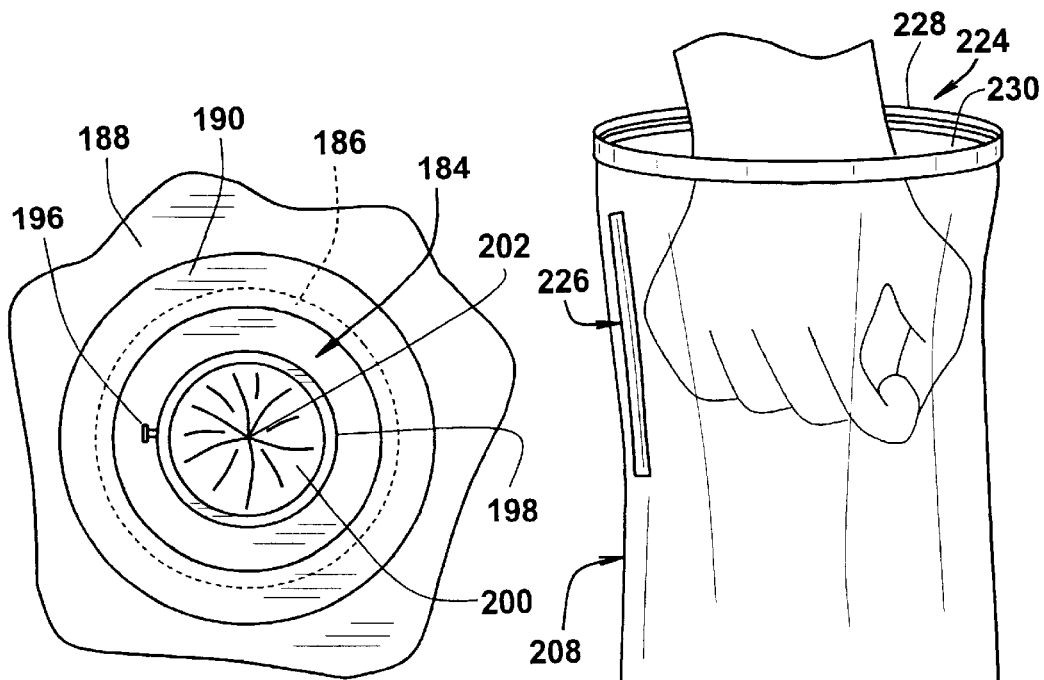

FIGS. 24 and 25 show a further embodiment of the apparatus where the envelope of the apparatus is secured to the body tissue on the exterior surface of the tissue surrounding the incision. Referring to FIG. 24, this embodiment is comprised of an envelope 184 having a wide circular base with a projecting annular rim 186. The rim 186 is secured to the exterior surface of the body tissue 188 by adhesive strips 190. Alternatively, the rim 186 may be secured to the tissue 188 by suturing or other equivalent means. The envelope 184 extends upwardly from its base and tapers toward a bellows section having a plurality of circular pleats 192. The tapering of the envelope gives it a general conical configuration with a larger interior volume of the envelope positioned adjacent its annular rim 186 than the volume of the envelope adjacent the pleats 192. The pleats 192 enhance the flexibility of the envelope allowing it to expand away from-the tissue incision 194 and compress toward the incision.

A port opening 196 passes through the side of the envelope just below the pleats 192. The port 196 is provided for gas insufflation of the body cavity accessible through the incision 194 and the interior volume of the envelope. A similar port may be provided on the envelopes of the previously described embodiments.

Just above the plurality of circular pleats 192 the distal end of the envelope is formed as a cylindrical sleeve 198. Positioned against the interior surface of the sleeve 198, is a valve 200 that seals closed around an instrument or a surgeon's hand inserted through the valve, or closes the center opening 202 of the valve when the instrument or hand is removed. The valve 200 may be a toroid of foam secured to the interior surface of the sleeve 198. The resilience of the foam enables its center opening 202 to expand when an instrument or the surgeon's hand is inserted through the opening, maintaining a sealed closure around the instrument or hand sufficient to maintain insufflation pressure in the body cavity and the envelope interior. The seal 200 may also be an inflatable bladder having a toroid shape which functions in the same manner as the foam toroid seal. Additionally, the toroid foam valve and the inflatable bladder toroid valve may be friction fit in and removable from the interior of the envelope sleeve 198. In this variation of the valve, it remains sealed around the hinge box of the surgical instrument or the surgeon's wrist as the instrument or wrist are removed from the interior of the envelope sleeve 198. In use of a valve of this type, the resilient material of the envelope 184 must be clamped closed by a surgical clamp as in previously described embodiments in order to maintain insufflation pressure in the body cavity as the instrument or wrist with attached seal are removed from the interior of the instrument sleeve 198. On reinsertion of the instrument or wrist with the attached seal back into the envelope interior with the toroid seal positioned in the envelope sleeve 198 interior, the clamp sealing closed the envelope may then be removed to permit access for the instrument through the tissue incision 194. The repositioned seal in the envelope sleeve 198 maintains insufflation pressure in the body cavity and the envelope interior.

Figure 26:
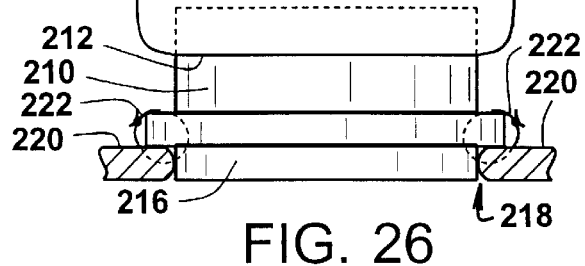
FIG. 26 shows a further embodiment of the invention.

FIG. 26 shows a still further embodiment of the apparatus of the invention. The embodiment of FIG. 26 is basically comprised of the flexible envelope 208 similar to previously described embodiments of the envelope, secured to a collar 210 which is also similar to previously described embodiments of the collar in FIGS. 1–23. The envelope 208 is shown permanently secured to the collar 210. However, the proximal end of the envelope 212 may be secured to the collar 210 in a variety of different manners such as the previously described embodiments. The upper end of the collar 210 may be inserted into the opening at the envelope proximal end 212 and the envelope secured around the collar by a cord such as a length of elastic tubing or a length of suture. The proximal end of the envelope may also be secured to the collar in other equivalent manners.

The collar 210 is similar to previously described embodiments of the second collar. It may also be releasably connected to a first collar such as that shown in FIGS. 1–4 and 5–8. Alternatively, the lower end 216 of the collar may be inserted directly into the tissue incision 218 as shown in FIG. 26. The incision 218 made through the body tissue 220 would be smaller than the periphery of the collar lower end 216 so that the tissue surrounding the incision is stretched to fit around the collar. The collar 210 would then be secured in place on the body tissue 220 and extending into the incision 218 by a plurality of sutures 222 passing through the tissue and the collar around the periphery of the collar. Alternatively, the collar could be secured in place extending into the incision by adhesive tape or other equivalent means.

The envelope 208 of the FIG. 26 embodiment differs from previously described embodiments in that a second opening 224 and a third opening 226 are provided in the envelope and are sealed closed by opposed tongue and groove flexible strips 228, 230, of the type employed on Ziploc® brand plastic bags. The opposed tongue 228 and groove 230 flexible strips, shown opened at the second opening 224 and closed at the third opening 226, provide two closures in the envelope 208 that are easily opened and closed as needed. Furthermore, in their closed positions they provide a sufficient seal to maintain insufflation pressure in the body cavity and the envelope interior. Providing the two tongue and groove closures at the second 224 and third 226 openings enables the surgeon's hand to be inserted through one opening and the opening sealed closed around the surgeon's wrist either by closing the tongue and groove strips or securing the envelope adjacent the second opening closed around the surgeon's wrist with a flexible cord as employed in the previous embodiments. With the envelope secured closed around the surgeon's wrist, as different instruments are needed by the surgeon these instruments can be removed from the envelope interior and inserted into the interior where they can be grasped by the surgeon's hand through the third opening 226.

Each of the later described embodiments of the invention is used in the same manner as the first described embodiment in providing access for a hand or instrument through a body tissue incision while maintaining insufflation pressure or a pneumoperitoneum within the body. Additionally, the apparatus of the invention may be employed by containing each of the instruments intended to be used in a minimally invasive surgical operation within their own envelope of the apparatus. The second collar 4 of each envelope would then enable the instruments, contained in their own envelope, to be quickly connected with the first collar 2 as needed during the course of the operation. The first collar 2 would be provided with a valve structure in its interior, for example, a stricture or some other equivalent type of valve within the interior bore of the first elastomeric collar to close and seal the bore as instruments in their own envelopes are removed from and attached to the first collar. The quick connect releasable connection of the first and second collars described above may also be replaced by other known types of connections, for example, a bayonet-type connection that enable the first and second collars to be quickly connected and disconnected as desired. Furthermore, the size of the envelope can be substantially increased from that shown in the drawing figures so that several instruments needed to perform a particular operation may be contained in the one envelope. This would enable the surgeon to pick up and use the instruments contained in the envelope as needed without breaking the seal in the wall of the envelope or around the surgeon's wrist to remove instruments from the envelope or insert additional instruments into the envelope.

Figure 27:
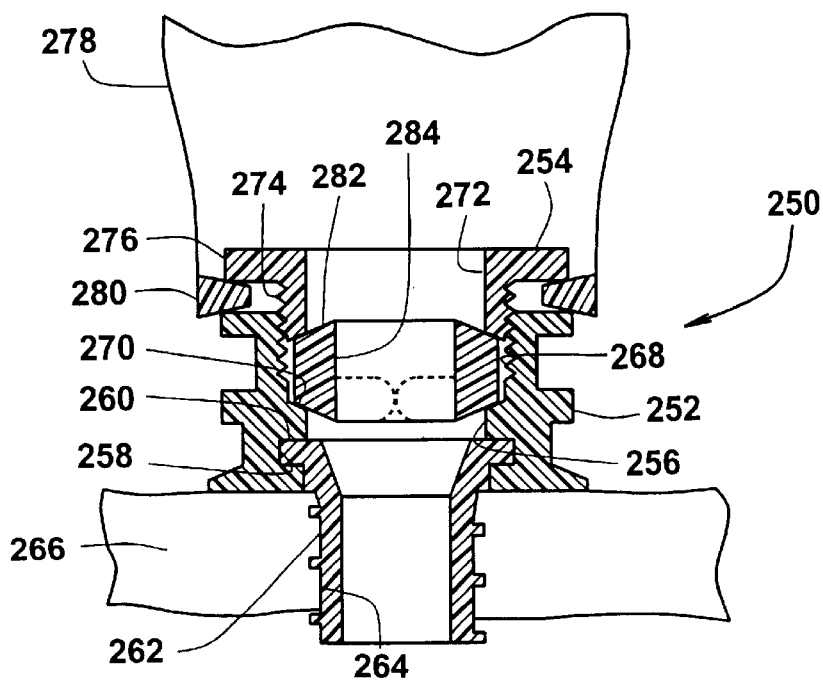
FIG. 27 shows the access port housing with an annular valve element.

FIG. 27 shows a further embodiment of the access port housing 250 which is comprised of a first housing member 252 and a second housing member 254. The first housing member 252 preferably has a cylindrical configuration with a cylindrical access opening 256 extending therethrough. An annular groove 258 is formed in the interior of the first housing opening 256 and an annular flange 260 of a skin screw 262 is received in the annular groove. The engagement of the flange in the groove secures the skin screw 262 to the access port housing 250. As described with reference to the embodiment of FIGS. 1–3, the skin screw 262 is turned in the incision 264 through the body tissue 266 to secure the access port housing 250 to the tissue over the incision. The cylindrical interior surface of the first housing member opening 256 also has interior screw threads 268 formed in the interior surface of the access opening adjacent the top of the housing member. Just below the interior screw threads is an annular shoulder 270 formed in the interior surface of the opening.

The second housing member 254 also has a cylindrical configuration and a cylindrical access opening 272 extending through its interior. The access opening 272 of the second member has substantially the same size diameter as the access opening 256 of the first housing member. Exterior screw threads 274 are formed on the outside of the second housing member. The exterior screw threads are complimentary to the interior screw threads of the first housing member. A flange 276 projects beyond the exterior screw threads at the top of the second housing member. The flange 276 preferably has a hexagonal configuration that facilitates manually turning the flange and the second housing member.

An envelope sleeve 278, such as any one of the previously described embodiments of the sleeve or the yet to be described embodiments, is attached to the access port housing 250 between the first and second housing members. The sleeve 278 has an annular ring 280 secured at its proximal opening. The annular ring 280 fits between the top surface of the first housing member 252 and the bottom surface of the second housing member flange 276. The annular ring 280 is resilient and compressible, providing a sealed connection between the sleeve and the access port housing.

An annular valve element 282 is positioned in the access opening of the access port housing between the first and second housing members. The annular valve element 282 is constructed of a compressible, resilient material. An inlet opening 284 passes through the valve element 282. By selectively turning the second housing member 254 so that it is screwed downwardly toward the first housing member 252, the annular valve element 282 is compressed within the access opening of the access port housing. Compressing the annular valve element between the two housing members causes the inlet opening 284 of the element to constrict, closing the inlet opening. The constricted, closed inlet opening is represented by dashed lines in FIG. 27. By turning the second housing member 254 so that it moves away from the first housing member 252, the resiliency of the annular valve element 282 causes it to resume its uncompressed configuration shown in FIG. 27, thereby opening the inlet opening 284. In this manner, the access port housing 250 selectively opens and closes access to the body tissue incision 264.

Figure 28:
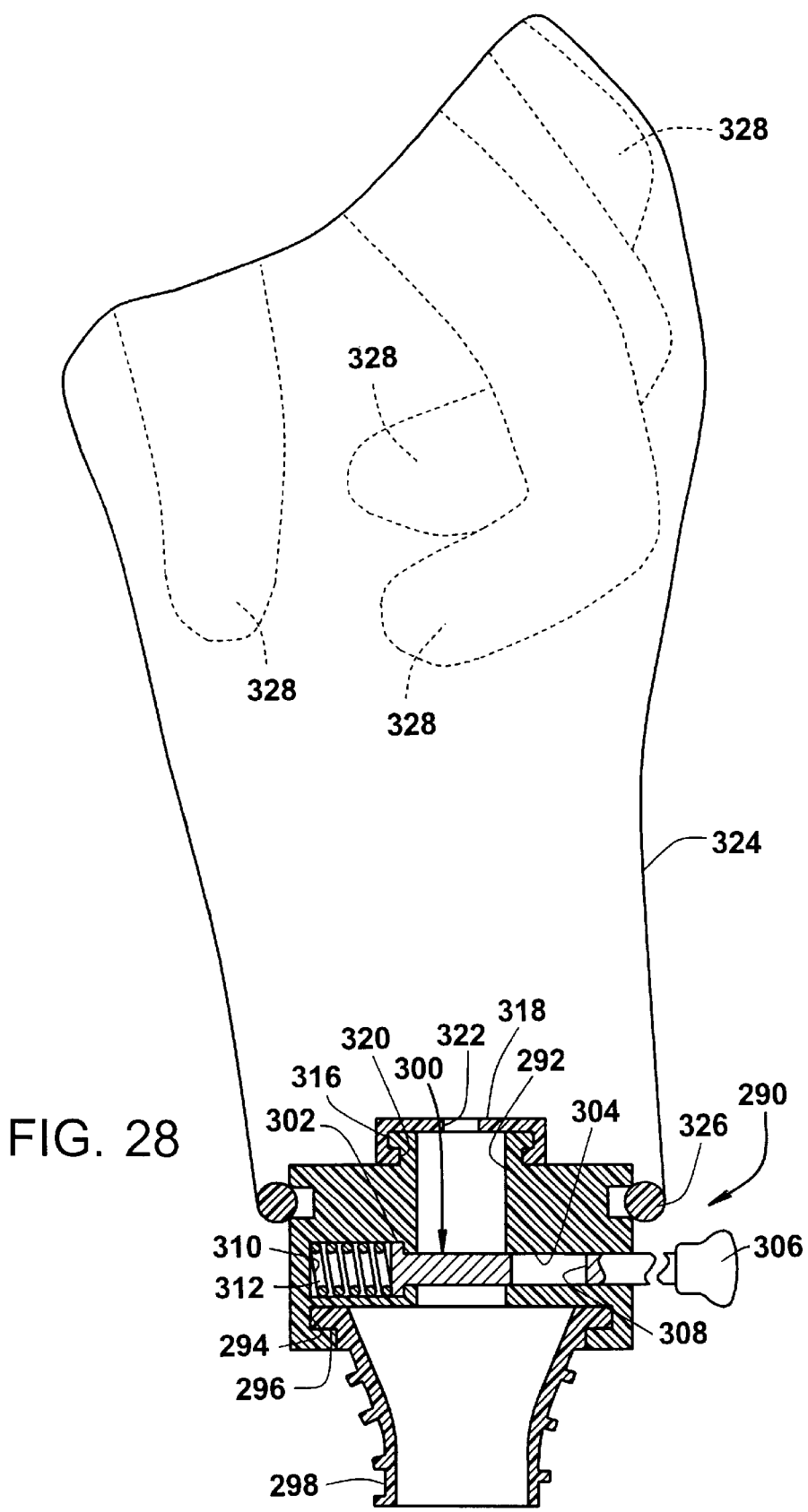
FIG. 28 shows the access port housing with a gate valve and an inverted glove envelope.

FIG. 28 shows a further embodiment of the access port housing 290. This housing also has a cylindrical configuration with a cylindrical access opening 292 extending through the center of the housing. An annular groove 294 is formed in the interior surface of the housing access opening and an annular flange 296 of a skin screw 298 is received in the annular groove. The engagement of the annular flange 296 in the annular groove 294 secures the skin screw to the access port housing.

A gate valve element 300 is mounted in the housing 290 and selectively opens and closes access through the housing access opening 292. The gate valve element is a planer member having a width larger than the diameter of the housing access opening 292. The length of the gate valve extends from a T-shaped ridge 302 at its rearward end or left hand end as viewed in FIG. 28, through a horizontal slot 304 having a rectangular cross section corresponding to the rectangular cross section of the gate valve, to a manual knob 306 at the forward end of the gate valve positioned outside the access port housing. The gate has an inlet opening 308 passing therethrough. The inlet opening 308 is circular and of the same size as the housing access opening 292. It is positioned on the gate so that, in the at rest position of the gate, the inlet opening is displaced from the housing access opening as shown in FIG. 28, thereby blocking access to the incision through the access opening. The T-shaped ridge 302 of the gate is positioned within a rectangular chamber 310 in the access port housing. The chamber is dimensioned sufficiently large to enable the T-shaped ridge 302 to be reciprocated through a portion of the chamber, and thereby reciprocating the gate valve 300 through the horizontal slot 304 in the access port housing. A spring 312 biases the gate valve to the right as viewed in FIG. 28. The chamber 310 is sufficiently large to enable manual manipulation of the knob 306 causing the gate valve to move to the left a sufficient distance to align the cylindrical access opening 292 of the housing with the inlet opening 308 of the gate valve. The inlet opening 308 has a diameter that matches that of the access opening 292 and when aligned with the access opening, provides access through the housing 290 and through the skin screw 298 and the tissue incision. Releasing the manual knob 306 causes the gate valve to move to the right to its at rest position shown in FIG. 28 under the bias of the spring 312, thereby closing the housing access opening 292.

An annular flange 316 is provided at the top of the housing 290 surrounding the access opening 292. A flexible instrument seal 318 is positioned over the annular flange. The seal has an inwardly projecting annular flange 320 that engages underneath the annular flange 316 of the housing to securely hold the seal over the housing access opening 292. An opening 322 passes through the center of the instrument seal. The opening 322 is dimensioned much smaller than the access opening 292 of the housing. The instrument seal 318 is constructed of a stretchable, resilient material that enables the seal opening 322 to expand when a surgical instrument is inserted through the opening. The stretching of the seal 318 around the instrument inserted through the seal opening 322 provides access through the seal while sealing around the instrument, thereby maintaining insufflation pressure in the body cavity. When the gate valve is moved to its open position to the left as viewed in FIG. 28, a surgical instrument may then be inserted through the seal opening and the housing into the tissue incision.

An envelope 324 similar to previously described embodiments of the envelopes is secured to the exterior of the port housing 290. The envelope has an opening at one end with an elastic, resilient ring 326 secured around the opening. The ring 326 may be an elastic band, an O ring, or other equivalent mechanism that can be employed to secure the opening of the envelope 324 around the access port housing 290.

As in previous embodiments, the envelope 324 has a general tubular, sleeve configuration except that the opposite end of the envelope from the port housing 290 does not have an opening. The envelope 324 is closed at its opposite end and has five inverted finger shaped appendages 328 formed in the envelope and extending into the interior volume of the envelope. The appendages 328 are dimensioned to receive the five fingers of either hand of the surgeon therein. They enable the surgeon to manipulate an instrument within the interior volume of the envelope 324 without requiring a second opening in the envelope that must be sealed around the surgeon's arm or the instrument as in previous embodiments of the envelope.

Figure 29:
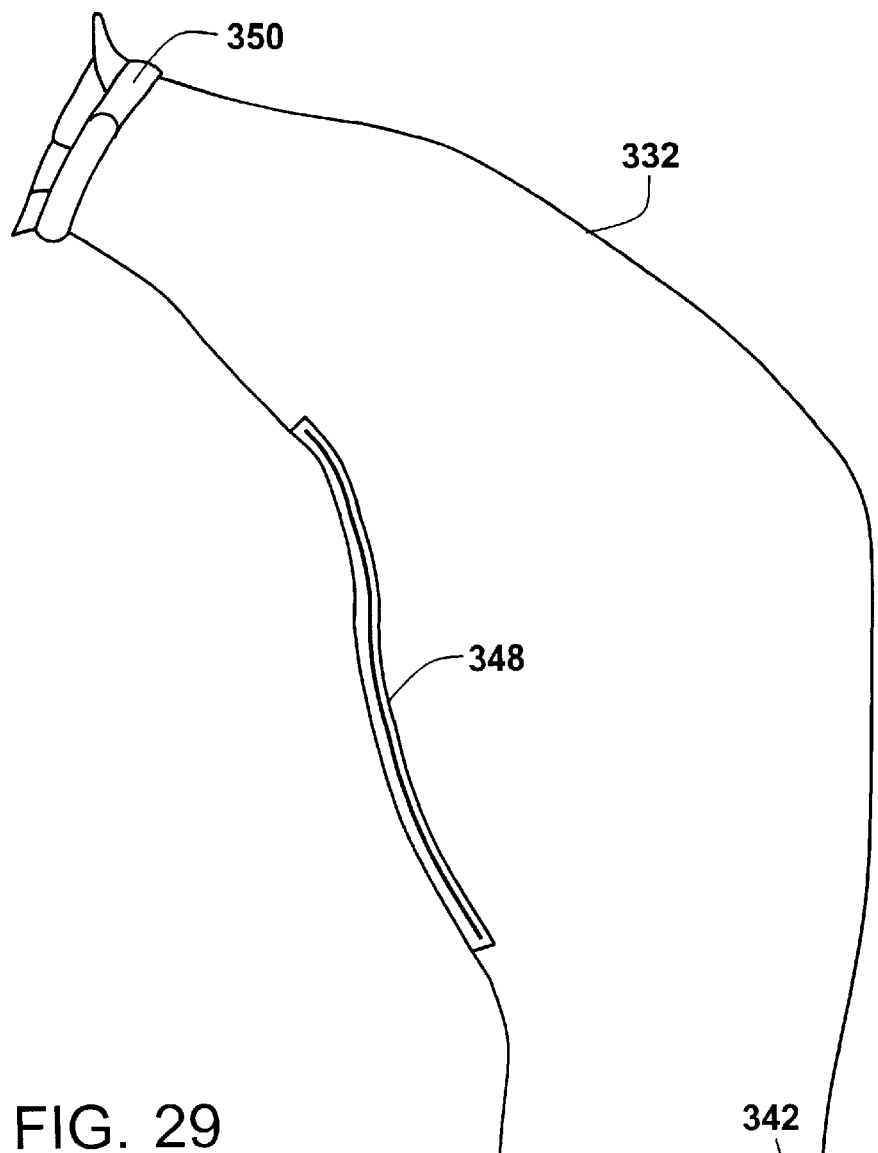
FIG. 29 shows the access port housing with a plug valve and an attached envelope having two openings.

FIG. 29 shows a further embodiment of the access port housing 330 and an additional embodiment of the envelope 332.

The access port housing 330 is similar to the embodiment of the housing shown in FIG. 28. The housing also has a cylindrical configuration with a skin screw 334 secured to the lower end of the housing substantially in the same manner as that of the previously described embodiment of FIG. 28. A generally cylindrical access opening 336 passes through the housing and expands as it extends from the top of the housing to the bottom of the housing. An annular flange 338 surrounds the access opening at the top of the housing and an instrument seal 340 is secured over the flange in the same manner as the previously described embodiment.

The FIG. 29 embodiment of the access port housing 330 differs from that of the FIG. 28 embodiment in that it does not include a gate valve and its related structure. Instead, the instrument seal 340 of the FIG. 29 embodiment is provided with a plug 342 secured to the seal by a tether 344. The plug 342 is dimensioned to sealingly seat in the seal opening 346 of the instrument seal, thereby closing the seal opening and maintaining insufflation pressure in the body cavity. The plug 342 is dimensioned sufficiently large to be easily inserted into the seal opening to close access through the access port housing, and to be manually removed from the opening providing access through the housing. The instrument seal 340 is constructed of flexible, resilient material that enables the seal opening 346 to stretch around an instrument inserted through the opening, thereby provided access through the opening while sealing around the instrument.

The envelope 332 is similar to that of the envelope embodiment shown in FIG. 26 except that the envelope 332 has only one zip-type closure 348 at the side of the envelope intermediate its ends, and has a VELCRO® type closure 350 around the end of the envelope opposite the access port housing 330. As in previous embodiments, the envelope has a generally tubular, sleeve configuration. The end of the envelope opposite the VELCRO® type closure 350 is secured to a cylindrical collar 352 having a radially outwardly projecting annular flange 354. The collar 352 extends around the opening to the envelope. An annular cap 356 is mounted on the collar 352 for rotation of the cap relative to the collar. The cap has a set of threads 358 formed in its interior surface. A complimentary set of threads 360 are formed around the exterior surface of the access port housing 330. Engagement of the threads of the annular cap 356 over the threads 358 of the housing removably attaches the envelope to the housing.

Figure 30:
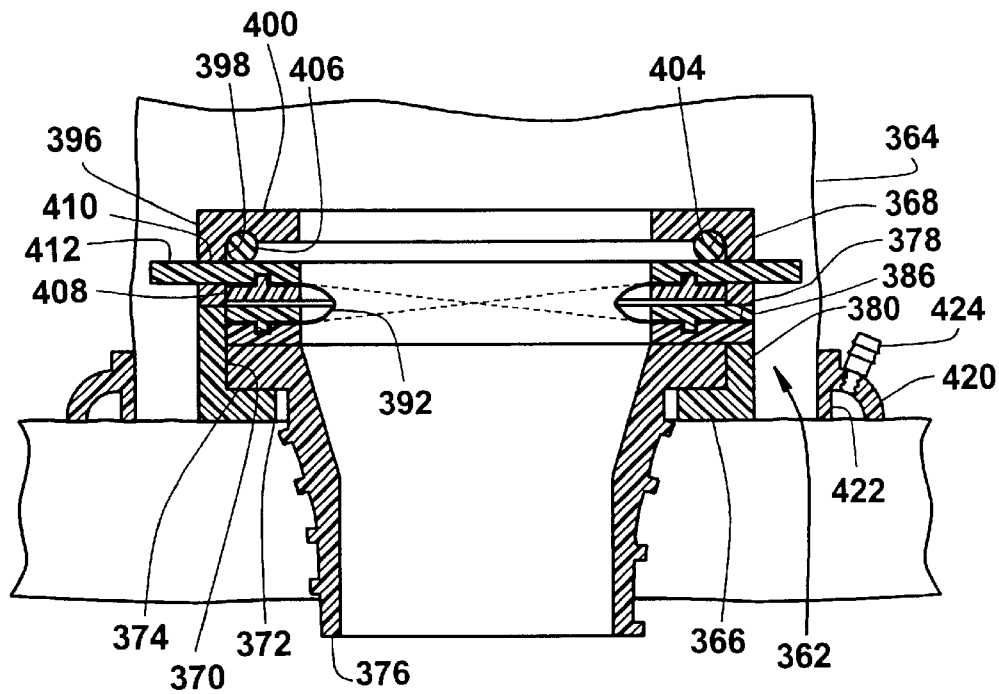
FIG. 30 shows the access port housing with an iris valve.
Figure 31:
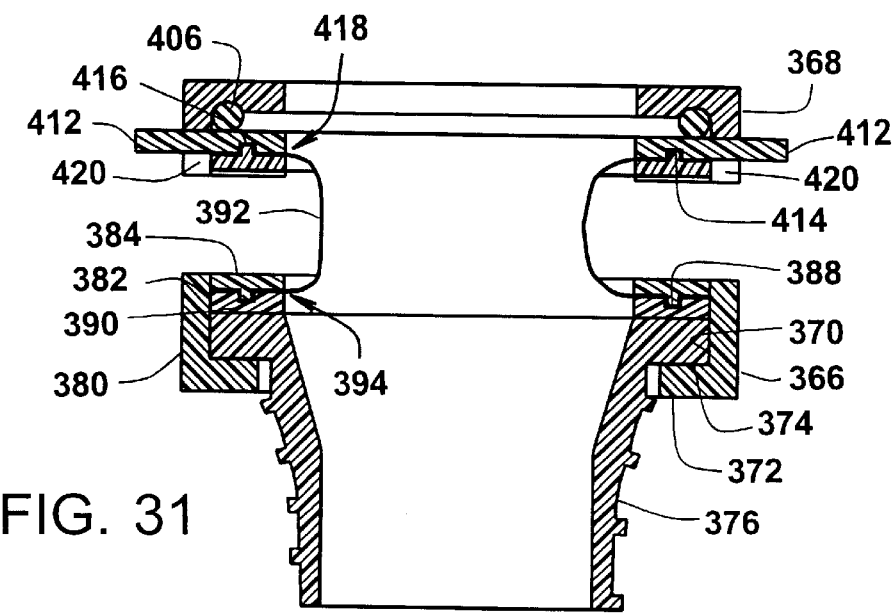
FIGS. 31 and 32 show details of the construction of the iris valve.
Figure 32:
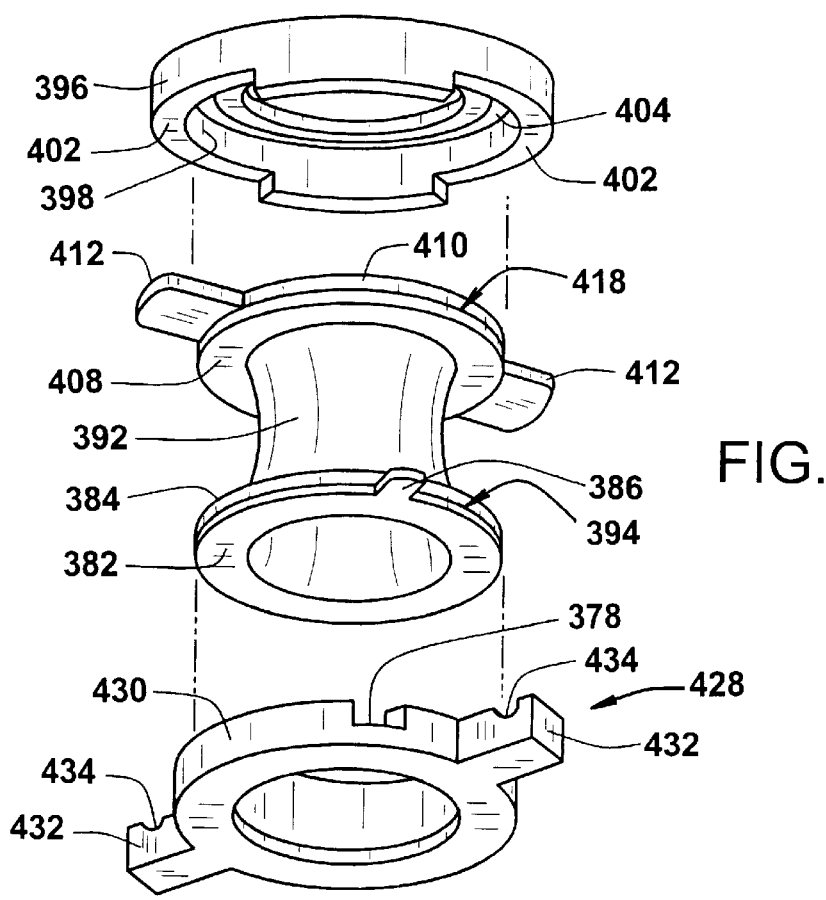

FIGS. 30–32 show a further embodiment of the access port housing 362 of the invention. This embodiment of the access port housing may be employed with any embodiment of the envelope, but may also be used without an attached envelope. The access port housing 362 shown in FIG. 30 is shown used with a further embodiment of the envelope 364 that is not attached to the access port housing as will be explained.

The access port housing 362 is comprised of a first housing member 366 and a second housing member 368. FIGS. 30, 31 and 32 show variations of the first housing member that differ only slightly from each other. In the embodiment shown in FIGS. 30 and 31, the first housing member 366 has a cylindrical configuration with a cylindrical interior surface 370 and an annular flange 372 that projects radially inwardly a slight distance from the bottom of the housing member. The flange 372 provides an abutment surface for the annular flange 374 of a skin screw 376. The skin screw 376 is employed to secure the access port housing 362 to the tissue incision positioned over the tissue incision. A small notch 378 is provided in the cylindrical sidewall 380 of the first housing member.

A first annular member is secured within the cylindrical sidewall 380 of the first housing member 366. The first annular member is comprised of a bottom ring 382 and a top ring 384. The two rings are substantially identical to each other except that the bottom ring 382 has a projecting tab 386 and an annular groove 388 in its top surface. The top ring has a projecting annular ridge 390 that is dimensioned to be received in the annular groove 388 of the bottom ring.

A tubular, flexible and resilient sleeve 392 is secured to the first annular member. The sleeve has opposite first and second ends. The first end 394 is stretched between the bottom ring 382 and top ring 384 of the first annular member and is secured therebetween with the annular projecting ridge 390 inserted into the annular groove 388 of the members. The first end of the sleeve 394 may be secured between the bottom ring and top ring of the first annular member by adhesives or other equivalent methods. The first annular member is then inserted into the cylindrical sidewall 380 of the first housing member 366 with the projecting tab 386 engaged in the notch 378 of the first housing member. The engagement of the tab in the notch secures the first annular member stationary relative to the first housing member 366.

The second housing member 368 is similar to the first housing member in that it has a cylindrical configuration substantially the same size as that as the first housing member. The second housing member has a cylindrical sidewall 396 with a cylindrical interior surface 398. An annular flange 400 projects inwardly from the cylindrical sidewall 396 at the top of the second housing member. A pair of arcuate notches 402 are formed in the cylindrical sidewall 396 opposite the annular flange 400. In the preferred embodiment, the arcuate notches 302 are positioned directly opposite each other and extend through 120° of the circumference of the cylindrical sidewall. Within the second housing member, where the cylindrical sidewall interior surface 398 joins the interior surface of the annular flange 400, a circular recess 404 is formed. An O-ring 406 is received in the circular recess 404.

A second annular member is mounted for rotation within the second housing member 368. The second annular member is comprised of a bottom ring 408 and a top ring 410. The bottom ring and top ring of the second annular member are similar to the bottom ring and top ring of the first annular member, except that the top ring 410 has a pair of projecting tabs 412 on opposite sides of the ring. The top ring 410 also has an annular groove 414 formed in its underside. The bottom ring 408 has an annular ridge 416 formed on its top surface that is dimensioned to be received in the annular groove 414 of the top ring.

The second end 418 of the tubular sleeve 392 is stretched between the second annular member top ring 410 and bottom ring 408 and is secured therebetween by the engagement of the annular projecting ridge 416 in the annular groove 414. The top and bottom rings of a second annular member may be secured together by adhesives or other equivalent methods, thereby securing the second end of the tubular sleeve between the two rings. The top and bottom rings 410, 408 of the second annular member are assembled into the cylindrical sidewall 396 of the second housing member 368 with the opposed projecting tabs 412 positioned within the arcuate notches 402. The top surface of the top ring 410 engages against the O-ring 406 forming a seal between the second housing member 368 and the second annular member. This positioning of the second annular member in the second housing member enables the second annular member to be rotated through 120 degrees relative to the second housing member.

The second housing member 368 is assembled to the first housing member 366 as shown in FIGS. 30 and 32. The two housing members may be secured together by adhesives, mechanical fasteners such as screws, or by other equivalent methods. With the first and second housing members assemble together, the first annular member formed by the top ring 384 and bottom ring 382 is held stationary within the access port housing 362. The second annular member formed by the top ring 410 and the bottom ring 408 is capable of being rotated through 120° between first and second positions of the second annular member relative to the access port housing. The first position of the second annular member relative to the access port housing is shown in FIG. 30. In this position, the interior of the tubular sleeve 392 forms an inlet opening through the access port housing providing access from the exterior of the housing through the tissue incision by way of the skin screw 376. When the second annular member comprised of the top ring 410 and bottom ring 408 is rotated to its second position relative to the access port housing, the tubular sleeve 392 is twisted about its center inlet opening and closes the inlet opening. Alternatively, with an object inserted through the inlet opening of the access port housing 362, when the second annular member, comprised of the top ring 410 and bottom ring 408, is twisted to its second relative position to the housing, the tubular sleeve 392 is twisted around the object inserted through the inlet opening, thereby constricting the sleeve around the object and sealing the sleeve around the object. In this manner, the valve element formed by the first and second annular members of the access port housing 362 selectively opens and closes access through the tissue incision by way of the inlet opening.

The embodiment of the envelope 364 shown in FIG. 30 is the same as previously described embodiments of the envelope except for the manner in which it is secured around the tissue incision. In the embodiment of FIG. 30, the envelope 364 is provided with an annular suction ring 420 that surrounds the access port housing 362. The suction ring has an annular groove 422 that extends around its underside. A suction stem 424 is secured to the annular ring 420 and communicates with the annular groove 422. In use, the annular suction ring 420 is positioned on the body tissue surrounding the incision as shown in FIG. 30. A source of vacuum pressure is then communicated with the suction stem 424, creating a suction vacuum pressure within the annular groove 422 of the ring. The suction vacuum pressure securely holds the annular ring 420 to the tissue surface, thereby securing the envelope 364 to the tissue surface.

As stated earlier, the embodiment of the access port housing shown in FIG. 32 differs from that of FIGS. 30 and 31 only in the construction of the first housing member. The remaining construction of the access port housing shown in FIG. 32 is the same as that shown in FIG. 1. The first housing member 428 of this embodiment does not employ the skin screw 376 to securely attach the access port housing over the incision. Therefore, the cylindrical sidewalls 430 of this first housing member need not be as large as that of the embodiment of FIG. 31 because they do not require receiving the annular flange 374 of the skin screw therein. Instead, the exterior of the first housing member 428 is provided with a pair of oppositely projecting arms 432. Notches 434 are provided in the top surfaces of the arms. In securing this embodiment of the access port housing to the body tissue surrounding the incision, the projecting arms 432 are sutured to the body tissue with suture being looped through the notches 434 of each of the arms. In this manner, the first housing member 428 of this embodiment of the access port housing is securely held over the tissue incision.

Although the invention has been described by reference to specific embodiments, it should be understood that other variations and adaptations of the invention can be made without departing from the intended scope of the invention defined by the following claims.

What is claimed is:

1. Surgical apparatus for providing access to a body cavity of a patient through an incision, the apparatus comprising:

an elongate component defining a passageway for providing access to the body cavity through the incision;

a member carried by the elongate component, the member having a surface configured to engage skin of the patient and the member defining a channel in the shape of a ring formed in the surface; and a fitting carried by the member, the fitting defining a passage in fluid communication with the channel.

2. The apparatus of claim 1, wherein the channel is sized and configured to encircle the incision.

3. The apparatus of claim 1, wherein the fitting is a suction stem configured for connection to a suction source.

4. The apparatus of claim 1, further comprising a suction source in fluid communication with the fitting.

5. The apparatus of claim 1, wherein the ring is substantially round.

6. The apparatus of claim 1, wherein the elongate component is a sleeve.

7. The apparatus of claim 6, wherein the passageway of the sleeve is sized to accommodate a medical practitioner's hand.

8. The apparatus of claim 7, wherein the sleeve includes a glove opposite the member.

9. Surgical apparatus for providing access to a body cavity of a patient through an incision, the apparatus comprising:

a sleeve defining a passageway for providing access to the body cavity through the incision;

a member attached to the sleeve, the member having a patient-contacting surface with a groove formed therein to surround the incision; and a fitting on the member having a passage in fluid communication with the groove.

10. The apparatus of claim 9, wherein the groove is an annular groove.

11. The apparatus of claim 10, wherein the annular groove is in the shape of a ring.

12. The apparatus of claim 11, wherein the ring is substantially circular.

13. The apparatus of claim 9, wherein the passageway of the sleeve is sized to accommodate a medical practitioner's hand.

14. The apparatus of claim 13, wherein the sleeve includes a glove opposite the member.

15. The apparatus of claim 9, wherein the fitting is a suction stem configured for connection to a suction source.

16. The apparatus of claim 9, further comprising a suction source in fluid communication with the fitting.

* * * * *

UNITED STATES PATENT AND TRADEMARK OFFICE
CERTIFICATE OF CORRECTION

PATENT NO.      : 6,315,770 B1
DATED           : November 13, 2001
INVENTOR(S)     : James Stephen Scott, Janine C. Robinson and Roger A. De La Torre It is certified that error appears in the above-identified patent and that said Letters Patent is hereby corrected as shown below:

Column 1,
Line 20, replace "cavity-requires" with -- cavity requires --.

Column 8,
Line 49, after "the" delete -- Y --.

Signed and Sealed this

Thirteenth Day of August, 2002

Attest:

JAMES E. ROGAN
Attesting Officer        Director of the United States Patent and Trademark Office

UNITED STATES PATENT AND TRADEMARK OFFICE
CERTIFICATE OF CORRECTION

| | | |
|---|---|---|
| PATENT NO. | : 6,315,770 B1 | Page 1 of 1 |
| DATED | : November 13, 2001 | |
| INVENTOR(S) | : James Stephen Scott, Janine C. Robinson and Roger A. De La Torre | |

It is certified that error appears in the above-identified patent and that said Letters Patent is hereby corrected as shown below:

<u>Column 18,</u>
Line 4, after "channel" insert -- wherein the elongate component is configured to be inverted through the passageway to access the body cavity --.
Line 92, after "groove" insert -- wherein the sleeve is configured to be inverted through the passageway to access the body cavity --.

Signed and Sealed this

Twenty-sixth Day of November, 2002

*Attest:*

*Attesting Officer*

JAMES E. ROGAN
*Director of the United States Patent and Trademark Office*